United States Patent [19]

Eistetter et al.

[11] 4,333,942
[45] Jun. 8, 1982

[54] ANTI-DEPRESSANT AND ANALGESIC 4-PHENOXYPIPERIDINES

[75] Inventors: Klaus Eistetter, Constance; Hans-Peter Kley, Allensbach; Heinz-Günter Menge; Hartmann Schaefer, both of Constance, all of Fed. Rep. of Germany

[73] Assignee: BYK Gulden Lomberg Chemische Fabrik GmbH, Constance, Fed. Rep. of Germany

[21] Appl. No.: 167,628

[22] Filed: Jul. 11, 1980

[30] Foreign Application Priority Data

Aug. 3, 1979 [CH] Switzerland .......................... 7127/79

[51] Int. Cl.³ .................. A61K 31/445; C07D 211/52; C07D 211/48
[52] U.S. Cl. .................................... 424/267; 546/216; 546/217; 546/221
[58] Field of Search ...................... 546/216, 217, 221; 424/267

[56] References Cited

U.S. PATENT DOCUMENTS 3,260,723 7/1966 L'Italien et al. ................. 546/216
3,438,991 4/1969 Janssen ................. 546/216
3,506,671 4/1970 Kaiser et al. ................. 424/267 X
3,551,433 12/1970 Hydro et al. ................. 546/216
4,216,218 8/1980 Klioze et al. ................. 546/216 X

FOREIGN PATENT DOCUMENTS 1289529 10/1969 Fed. Rep. of Germany .
2822307 12/1978 Fed. Rep. of Germany .

1799M 4/1963 France .

OTHER PUBLICATIONS

Derwent Abstract of Belgian Patent 857,481 (8/76).

Primary Examiner—Richard A. Schwartz
Attorney, Agent, or Firm—Berman, Aisenberg & Platt

[57] ABSTRACT

4-Phenoxypiperidines of the general formula I

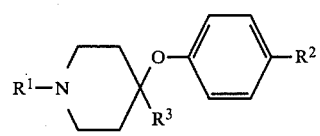

(I)

wherein
  $R^1$ denotes a hydrogen atom, an alkyl group with 1 to 5 carbon atoms, an alkenyl group with 3 to 5 carbon atoms, a cycloalkylmethyl group with 3 to 7 carbon atoms in the cycloalkyl part or a phenylalkyl group with 1 to 3 carbon atoms in the alkyl part,
  $R^2$ denotes a hydrogen atom, a nitro group, an amino group or an acylamino group and
  $R^3$ denotes a phenyl group or a benzyl group,
and their N-oxides and their acid-addition salts are new compounds. They have an antiptotic and analgesic action and are suitable for the treatment of depressions and painful conditions. Processes for the preparation of the new compounds are provided.

28 Claims, No Drawings

ANTI-DEPRESSANT AND ANALGESIC 4-PHENOXYPIPERIDINES

TECHNICAL FIELD

The invention relates to 4-phenoxypiperidines, processes for their preparation, their use and medicaments containing them.

The compounds according to the invention are used in the pharmaceutical industry as pharmacologically-active ingredients, as intermediate products and for the preparation of medicaments.

BACKGROUND

4-Phenylpiperidines, which have an antidepressive, anti-aggressive, diuretic, anti-Parkinson, bronchodilatory and anti-arthritic activity, are described in German Offenlegungsschrift DE-OS No. 2,735,051. Significant to the pharmacological activity of these compounds is the presence of a hydroxyl group, or an ester derivative thereof, in the 3-position of the piperidine ring; esterified hydroxyl groups in the 3-position and 4-position of the piperidine ring are stated to be of particular importance. In contrast, certain 4-phenoxypiperidines which are unsubstituted in the 3-position now display pharmacologically-interesting and specific properties.

THE INVENTION

The invention relates to 4-phenoxypiperidines (which are free from hydroxy or etherified hydroxy in the 3-position) of formula I

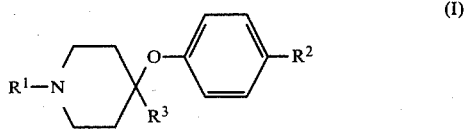

wherein
  $R^1$ denotes a hydrogen atom (—H), alkyl with from 1 to 5 carbon atoms, alkenyl with from 3 to 5 carbon atoms, cycloalkylmethyl with from 3 to 7 ring carbon atoms or phenylalkyl with from 1 to 3 carbon atoms in the alkyl part,
  $R^2$ denotes a hydrogen atom (—H), nitro, an amino group or an acylamino group and
  $R^3$ denotes phenyl or benzyl,
and their N-oxides and their acid-addition salts.

Alkyl and alkenyl groups are straight-chain or branched. Examples of alkyl groups are methyl, ethyl, propyl, isopropyl, isobutyl, sec.-butyl, tert.-butyl, neopentyl and tert.-pentyl groups; examples of alkenyl groups are allyl and 2-methylallyl. The methyl, tert.-butyl and allyl groups are preferred.

Examples of cycloalkylmethyl are cyclobutylmethyl, cycloheptylmethyl, cyclohexylmethyl, cyclopentylmethyl and cyclopropylmethyl. The cyclopropylmethyl group is preferred.

Examples of phenylalkyl are benzyl, 1-phenylethyl, 2-phenylethyl and 3-phenylpropyl. The benzyl group is preferred.

Amino includes —NH$_2$ and acylamino —NH-acyl.

Possible acyl radicals of the acylamino groups are the customary (carboxylic acid and carbonic acid) acyl groups used for protecting amino groups. Examples include lower alkylcarbonyl with, e.g., from 1 to 5 carbon atoms in the alkyl part, lower alkoxycarbonyl with, e.g., 1 or 2 carbon atoms in the alkoxy part and benzoyl optionally substituted by chloro, bromo, fluoro, methyl, trifluoromethyl or methoxy.

Contemplated salts include all the acid-addition salts. The pharmacologically-acceptable salts of the inorganic and organic acids customarily used galenically are of particular importance. Pharmacologically-unacceptable salts are readily converted into pharmacologically-acceptable salts by processes which are known to the artisan. Examples of pharmacologically-acceptable salts are water-soluble or water-insoluble acid-addition salts, such as the hydrochloride, hydrobromide, hydroiodide, phosphate, nitrate, sulfate, acetate, citrate, gluconate, benzoate, hibenzate {[2-(4-hydroxybenzoyl)]benzoate}, propionate, butyrate, sulfosalicylate, maleate, laurate, malate, fumarate, succinate, oxalate, tartrate, amsonate (4,4'-diaminostilbene-2,2'-disulfonate), embonate [4,4'-methylene-bis-(3-hydroxy-2-naphthoate)], metembonate [4,4'-methylene-bis-(3-methoxy-2-naphthoate)], stearate, tosylate (p-toluenesulfonate), 2-hydroxy-3-naphthoate, 3-hydroxy-2-naphthoate, fendizoate (2-[(2'-hydroxy-4-biphenylyl)carbonyl]-benzoate) and mesylate (methanesulfonate).

A first group (Ia) of particular embodiments of formula I includes those compounds
wherein
  $R^1$ denotes a hydrogen atom, straight-chain alkyl with from 1 to 3 carbon atoms or phenylalkyl with 1 or 2 carbon atoms in the alkyl part,
  $R^2$ denotes a hydrogen atom (—H), nitro, an amino group or alkylcarbonylamino with from 1 to 5 carbon atoms in the alkyl part, and
  $R^3$ denotes phenyl or benzyl,
and their N-oxides and their acid-addition salts.

Preferred representatives (Ia1) of this group embodiment are those
in which
  $R^1$ denotes a hydrogen atom, methyl or benzyl,
  $R^2$ denotes a hydrogen atom, nitro or an amino group and
  $R^3$ denotes phenyl or benzyl,
and their N-oxides and their acid-addition salts.

Particularly preferred representatives (Ia2) of this group are those
in which
  $R^1$ denotes a hydrogen atom, methyl or benzyl,
  $R^2$ denotes a hydrogen atom, nitro or an amino group and
  $R^3$ denotes phenyl,
and their pharmacologically-acceptable acid-addition salts.

Selected representatives (Ia3) of this first group include those compounds
in which
  $R^1$ denotes a hydrogen atom, methyl or benzyl,
  $R^2$ denotes an amino group and
  $R^3$ denotes phenyl,
and their pharmacologically-acceptable acid-addition salts.

A second particular embodiment (Ib) of formula I encompasses those compounds
wherein
  $R^1$ denotes branched alkyl with from 3 to 5 carbon atoms, alkenyl with from 3 to 5 carbon atoms or cycloalkylmethyl with from 3 to 5 ring carbon atoms, $R^2$ denotes a hydrogen atom, nitro, an amino group or an alkylcarbonylamino group with from 1 to 5 carbon atoms in the alkyl part, and $R^3$ denotes phenyl or benzyl, and their N-oxides and their acid-addition salts.

Preferred representatives (Ib1) of this particular embodiment are those
in which $R^1$ denotes branched alkyl with from 3 to 5 carbon atoms, allyl or cyclopropylmethyl, $R^2$ denotes a hydrogen atom, nitro or an amino group and $R^3$ denotes phenyl or benzyl, and their N-oxides and their acid-addition salts.

Particularly preferred representatives (Ib2) of the second embodiment are those
in which $R^1$ denotes isopropyl or tert.-butyl, $R^2$ denotes a hydrogen atom, nitro or an amino group and $R^3$ denotes phenyl, and their pharmacologically-acceptable acid-addition salts.

Examples of representatives of compounds according to the invention are 1-ethyl-4-phenoxy-4-phenylpiperidine, 1-cyclobutylmethyl-4-phenoxy-4-phenylpiperidine, 1-isobutyl-4-phenoxy-4-phenylpiperidine, 1-(3-phenylpropyl)-4-phenoxy-4-phenylpiperidine, 1-neopentyl-4-phenoxy-4-phenylpiperidine, 1-benzyl-4-phenoxy-4-phenylpiperidine, 1-isopropyl-4-phenoxy-4-phenylpiperidine N-oxide, 1-(n-butyl)-4-benzyl-4-phenoxypiperidine, 4-benzyl-1-ethyl-4-phenoxypiperidine, 4-benzyl-1-cyclohexylmethyl-4-phenoxypiperidine, 4-benzyl-1-propyl-4-phenoxypiperidine, 4-benzyl-1-(sec.-butyl)-4-phenoxypiperidine, 4-benzyl-1-isopentyl-4-phenoxypiperidine, 4-benzyl-1-methyl-4-phenoxypiperidine N-oxide, 1-benzyl-4-(4-nitrophenoxy)-4-phenylpiperidine, 1-cyclopentylmethyl-4-(4-nitrophenoxy)-4-phenylpiperidine, 1-ethyl-4-(4-nitrophenoxy)-4-phenylpiperidine, 1-(n-butyl)-4-(4-nitrophenoxy)-4-phenylpiperidine, 1-(tert.-butyl)-4-(4-nitrophenoxy)-4-phenylpiperidine N-oxide, 1-neopentyl-4-(4-nitrophenoxy)-4-phenylpiperidine, 4-(4-nitrophenoxy)-4-phenyl-1-(3-phenylpropyl)piperidine, 1,4-dibenzyl-4-phenoxypiperidine, 4-benzyl-1-ethyl-4-phenoxypiperidine N-oxide, 4-benzyl-1-cyclopropylmethyl-4-phenoxypiperidine, 4-benzyl-1-isobutyl-4-phenoxypiperidine, 4-benzyl-1-isopentyl-4-phenoxypiperidine N-oxide, 4-benzyl-1-neopentyl-4-phenoxypiperidine, 4-benzyl-1-(n-butyl)-4-phenoxypiperidine N-oxide, 4-benzyl-4-phenoxypiperidine, 4-(4-aminophenoxy)-1-ethyl-4-phenylpiperidine, 4-(4-aminophenoxy)-1-cyclopropylmethyl-4-phenylpiperidine, 4-(4-aminophenoxy)-1-neopentyl-4-phenylpiperidine, 4-(4-aminophenoxy)-4-phenyl-1-(3-phenylpropyl)piperidine, 4-(4-aminophenoxy)-1-(n-butyl)-4-phenylpiperidine, 1-ethyl-4-(4-isobutyrylaminophenoxy)-4-phenylpiperidine, 1-isopropyl-4-phenyl-4-(4-propionylaminophenoxy)piperidine, 1-(n-butyl)-4-[4-(4-hexanoyl)aminophenoxy]-4-phenylpiperidine, 4-benzyl-1-ethyl-4-(4-isobutyrylaminophenoxy)piperidine, 4-benzyl-1-isopropyl-4-[4-(n-pentanoylamino)phenoxy]piperidine and 4-benzyl-1-ethyl-4-(4-propionylaminophenoxy)piperidine and their acid-addition salts.

Selected compounds according to the invention are 1-methyl-4-phenoxy-4-phenylpiperidine, 4-(4-aminophenoxy)-4-benzyl-1-methylpiperidine and, in particular, 4-(4-aminophenoxy)-1-methyl-4-phenylpiperidine and their pharmacologically-acceptable acid-addition salts.

The 4-phenoxypiperidines of formula I and of the first and second particular embodiments (Ia and Ib), their N-oxides and their acid-addition salts have valuable properties which render them commercially useful. On the one hand, the compounds, their N-oxides and their pharmacologically-, i.e. biologically-, acceptable acid-addition salts display a pronounced antiptotic action, which is coupled to a powerful analgesic action. On the other hand, the compounds are intermediate products for the preparation of pharmacologically-active 4-phenoxypiperidines.

Thus, for example, compounds of formula I in which $R^1$ denotes phenylalkyl, in particular benzyl, are readily converted into compounds of formula I in which $R^1$ represents a hydrogen atom (—H) by splitting off the phenylalkyl group. These latter compounds serve as valuable starting compounds for the preparation of derivatives of formula I in which $R^1$ represents alkyl, alkenyl or cycloalkylmethyl. 4-Phenoxypiperidines of formula I, wherein $R^2$ denotes nitro are intermediate products for the preparation of those compounds of formula I in which $R^2$ denotes amino, acylamino or a hydrogen atom.

The antiptotic effect of the compounds according to the invention is demonstrated by a powerful reserpine antagonism at a low dosage. The pronounced analgesic action is demonstrated on various animal analgesia models, and this action is antagonized by naloxone. The stimulating effect of the compounds according to the invention on the central nervous system is not antagonized by naloxone, but rather intensified, so that it must be concluded that, in mammals, different sites of action for the two effects are involved.

The excellent pharmacological activity of the compounds according to the invention makes them useful in human medicine as antidepressants and analgesic agents; they are useful for prophylaxis and, above all, for the treatment of symptoms which have already appeared.

Examples of indications in the field of human medicine, in men or women of any age, are depressions having various etiologies and symptomatologies, such as endogenic depressions, psychogenic depressions, exhaustion depressions and depressive psychoses; and painful conditions of various origin, in particular chronic painful conditions which lead to depressions or are associated therewith.

The invention thus furthermore relates to a process for the treatment of mammals suffering from one of the previously-mentioned illnesses. The process is characterized by administering a therapeutically-effective and pharmacologically-acceptable amount of one or more compounds of formula I or of a particular embodiment thereof and/or acid-addition salts and/or N-oxides thereof to an affected mammal.

The invention also relates to the use of compounds according to the invention in combating the previously-mentioned illnesses. The invention also relates to the use of compounds according to the invention in the preparation of medicaments which are employed for combating the noted illnesses.

The invention furthermore relates to medicaments which contain one or more 4-phenoxypiperidines of formula I
wherein $R^1$ denotes a hydrogen atom, alkyl with from 1 to 5 carbon atoms, alkenyl with from 3 to 5 carbon atoms, cycloalkylmethyl with from 3 to 7 ring carbon atoms or phenylalkyl with from 1 to 3 carbon atoms in the alkyl part, $R^2$ denotes a hydrogen atom, nitro, an amino group or acylamino and $R^3$ denotes phenyl or benzyl, and/or their pharmacologically-acceptable N-oxides and/or acid-addition salts.

Embodiments of the medicaments are those which contain pharmacologically-active and acceptable 4-phenoxypiperidines of the first or second embodiments or their preferred representatives, their N-oxides and/or their acid-addition salts.

The compounds according to the invention are formulated to give medicaments by conventional processes. As medicaments, the new compounds are employed as such or, if appropriate, in combination with suitable pharmaceutical excipients. When the new pharmaceutical formulations contain pharmaceutical excipients in addition to the active compounds, the content of active compound in these mixtures is from 5 to 95, preferably from 25 to 75, percent by weight of the total mixture.

In accordance with the invention the active compounds are used, in the field of human medicine, in any desired form, for example systemically, provided that the establishment and maintenance of sufficient levels of active compound in the blood or tissue are ensured. This is achieved by oral, rectal or parenteral administration in suitable doses. The pharmaceutical formulation of the active compound is advantageously in the form of unit doses appropriate for the desired administration. A unit dose is, for example, in the form of a tablet, a dragee, a capsule, a suppository or a measured volume of a powder, of a granular material, of a solution, of an emulsion, of a suspension, of a sol or of a gel.

"Unit dose" for the purpose of the present invention means a physically-determined unit which contains an individual amount of the active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or a one-quarter, of the unit dose is required for an individual therapeutic administration, the unit dose is advantageously divisible, for example, in the form of a tablet with a breaking groove.

When in the form of unit doses and intended, for example, for administration to humans, the pharmaceutical formulations according to the invention contain about 0.5 to 50 mg, advantageously 5 to 40 mg and in particular 10 to 30 mg, of active compound.

In general, it has proved advantageous in human medicine to administer the active compound or compounds, when these are given orally, in a daily dose of from about 1.0 to about 50 mg, preferably from 5 to 50 mg, and in particular from 10 to 30 mg, if appropriate in the form of several, preferably 1 to 3, individual administrations to achieve the desired results. An individual administration contains the active compound or compounds in amounts of from about 0.5 to about 25 mg, preferably from 3 to 15 mg and in particular from 5 to 10 mg.

In the case of long-term medication, the pharmaceutical formulation is generally administered, for therapeutic purposes, at fixed points in time, such as 1 to 3 times daily, for example after each meal and/or in the evening. In acute cases medication takes place at varying points in time. Under certain circumstances, it may be necessary to deviate from the dosages mentioned, and in particular to do so in accordance with the nature, body weight and age of the patient to be treated, the nature and severity of the illness, the nature of the formulation and of the administration of the medicament, and the time or interval over which administration takes place. Thus, in the case of therapy in small initial doses, it is appropriate to start with less than the noted amount of active compound and to achieve the previously-mentioned amount of active compound only in the course of treatment. The optimum dosage and method of administration of the active compounds required in each particular case can be determined by the expert at any time in accordance with his expert knowledge.

The pharmaceutical formulations as a rule consist of active compound according to the invention and non-toxic, pharmaceutically-acceptable medicinal excipients, which are used as an admixture or diluent in solid, semi-solid or liquid form, or as a means of encasing, for example in the form of a capsule, a tablet coating, a sachet or some other container for the therapeutically-active ingredient. An excipient can, for example, serve as a promoter of the resorption of the medicament by the body, as a formulating auxiliary, as a sweetener, as a flavor correctant, as a colorant or as a preservative.

Examples of forms which are orally useful are tablets, dragees, hard and soft capsules (for example, made of gelatin), dispersible powders, granules, aqueous and oily suspensions, emulsions, solutions or syrups.

Tablets optionally contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets are also optionally provided with a coating which, e.g., results in delayed dissolution and resorption of the medicament in the gastrointestinal tract and hence, for example, better tolerance, a protracted effect or a retarded effect. Gelatin capsules optionally contain the medicament mixed with a solid diluent, for example calcium carbonate or kaolin, or an oily diluent, for example olive oil, groundnut oil or paraffin oil.

Aqueous suspensions optionally contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitol monooleate, polyoxyethylene sorbitan monooleate or lecithin; preservatives, for example methyl hydroxybenzoate or propyl hydroxybenzoate; flavoring agents; and sweeteners, for example sucrose, lactose, sodium cyclamate, dextrose or invert sugar syrup.

Oily suspensions optionally contain, for example, groundnut oil, olive oil, sesame oil, coconut oil or paraffin oil, and thickeners, such as beeswax, hard paraffin or cetyl alcohol; and, furthermore, sweeteners, flavoring agents and antioxidants.

Water-dispersible powders and granules optionally contain the medicaments mixed with dispersing agents, wetting agents and suspending agents, for example those previously mentioned, as well as with sweeteners, flavoring agents and colorants.

Emulsions optionally contain, for example, olive oil, groundnut oil or paraffin oil, in addition to emulsifying agents, such as gum acacia, gum tragacanth, phosphatides, sorbitan monooleate or polyoxyethylene sorbitan monooleate, and sweeteners and flavoring agents.

For rectal administration of the medicaments, suppositories which are prepared with the aid of binders (which melt at rectal temperature, for example cacao butter or polyethylene glycols) are used.

For parenteral administration of the medicaments, sterile injectable aqueous solutions, for example isotonic salt solutions or other solutions which contain dispersing agents or wetting agents and/or pharmacologically-acceptable diluents, for example propylene glycol or butylene glycol, are used.

The active compound or compounds can also be in a microencapsulated form, if appropriate together with one or more of the previously-mentioned excipients.

In addition to the 4-phenoxypiperidines according to the invention, their pharmacologically-acceptable N-oxides or their acid-addition salts, the pharmaceutical formulations also optionally contain one or more pharmacologically-active ingredients from other groups of medicaments, for example mild stimulants, such as caffeine; analgesic agents, such as aminophenazone and acetylsalicylic acid; antiphlogistic agents, such as phenylbutazone, indomethacin and (hetero)arylacetic acids; minor tranquilizers, such as meprobamate, chlordiazepoxide and diazepam; major tranquilizers, such as perazine and fluophenazine; agents which stimulate cerebral blood flow and cerebral metabolism and/or tonics, such as glutamic acid, inorganic salts, vitamins and combinations thereof.

The invention furthermore relates to a process for the preparation of the 4-phenoxypiperidines of formula I wherein
$R^1$ denotes a hydrogen atom (—H), an alkyl group with from 1 to 5 carbon atoms, an alkenyl group with from 3 to 5 carbon atoms, a cycloalkylmethyl group with from 3 to 7 carbon atoms in the cycloalkyl part or a phenylalkyl group with from 1 to 3 carbon atoms in the alkyl part,
$R^2$ denotes a hydrogen atom (—H), a nitro group, an amino group or an acylamino group and
$R^3$ denotes a phenyl group or a benzyl group,
and their N-oxides and their acid-addition salts, which is characterized by reacting a) a 4-hydroxypiperidine of formula II

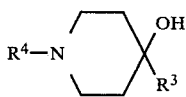

wherein
$R^3$ has its previously-indicated meaning and
$R^4$ denotes an alkyl group with from 1 to 5 carbon atoms, an alkenyl group with from 3 to 5 carbon atoms, a cycloalkylmethyl group with from 3 to 7 carbon atoms in the cycloalkyl part, a phenylalkyl group with from 1 to 3 carbon atoms in the alkyl part or a $R^5$—CO group and $R^5$ denotes a hydrogen atom (—H), an alkyl group with from 1 to 4 carbon atoms, an alkenyl group with from 2 to 4 carbon atoms, a cycloalkyl group with from 3 to 7 ring carbon atoms, a phenyl group or a phenylalkyl group with 1 or 2 carbon atoms in the alkyl part, or a salt thereof with (b) 4-nitrofluorobenzene in an aprotic solvent containing a strong base. The resulting reaction product is then optionally subjected to one or more of the following process steps:

(a) dealkylation of resulting compounds of formula I (wherein $R^1$ denotes an alkyl, alkenyl, cycloalkylmethyl or phenalkyl group) to obtain compounds of formula I wherein $R^1$ represents a hydrogen atom;

(b) deacylation of resulting compounds of formula I (wherein $R^1$ represents an $R^5$—CO—group) to obtain compounds of formula I wherein $R^1$ represents a hydrogen atom;

(c) alkylation of resulting compounds of formula I (wherein $R^1$ denotes a hydrogen atom) to obtain compounds of formula I wherein $R^1$ denotes an alkyl, alkenyl, cycloalkylmethyl or phenalkyl group;

(d) reduction of resulting compounds of formula I (wherein $R^1$ represents an $R^5$—CO—group) to obtain compounds of formula I wherein $R^1$ denotes an alkyl, alkenyl, cycloalkylmethyl or phenalkyl group;

(e) reduction of resulting compounds of formula I (wherein $R^2$ represents a nitro group) to obtain compounds of formula I wherein $R^2$ represents an amino group, and, optionally, subsequent acylation;

(f) reduction of resulting compounds of formula I (wherein $R^2$ represents an amino group) to obtain compounds of formula I wherein $R^2$ represents a hydrogen atom;

(g) conversion of the resulting base into an acid-addition salt or of a resulting acid-addition salt into the corresponding base; and (h) conversion of the resulting base or of an acid-addition salt into the corresponding N-oxide.

The reaction of a piperidinol II with 4-nitrofluorobenzene is carried out in an aprotic solvent, such as dimethylformamide, dimethylsulfoxide or hexamethylphosphoric acid triamide, preferably in dimethylformamide. Examples of strong bases are sodium hydride, potassium tert.-butylate, potassium tert.-amylate, n-butyl-lithium or naphthalene-sodium, preferably sodium hydride. The piperidinol II is transiently converted into the corresponding alcoholate at temperatures between 0° and 80° C., preferably at room temperature (about 20° C.). Etherification of II to obtain the 4-(4-nitrophenoxy)piperidine I is effected by subsequently adding 4-nitrofluorobenzene at temperatures between 0° and 100°, preferably at from 50° to 60° C.

The process steps which optionally follow are conventional.

The dealkylation (in which "alkyl" also includes: alkenyl, cycloalkylmethyl and phenylalkyl, in particular benzyl) is carried out, for example, with a chloroformic acid ester, such as chloroformic acid ethyl ester or chloroformic acid $\beta,\beta,\beta$-trichloroethyl ester, in the absence or presence of inert solvent, such as benzene, toluene or chloroform, at an elevated temperature, preferably at the boiling point of the solvent. The resulting intermediate product is reacted with aqueous or alcoholic solutions of bases, such as sodium hydroxide solution/ethanol or potassium hydroxide solution/butanol, at elevated temperature, preferably at the boiling point of the solvent, to obtain the corresponding dealkyl-4- phenoxypiperidine, that is to obtain a compound of formula I in which $R^1$ denotes a hydrogen atom.

Alternatively, dealkylation in the specific form of debenzylation, that is when resulting compounds of formula I (wherein $R^1$ denotes benzyl) are employed, is carried out by hydrogenolysis in the presence of a catalyst, preferably palladium-on-charcoal, in a solvent, such as methanol, ethanol, benzene or cyclohexane, at from 0° to 50°, preferably at room temperature, and under a hydrogen pressure of from 1 to 300 atmospheres, preferably of from 1 to 5 atmospheres.

The deacylation of resulting compounds of formula I (wherein $R^1$ denotes an $R^5$—CO—group) is carried out, for example, with aqueous or alcoholic solutions of bases, such as sodium hydroxide solution/ethanol or potassium hydroxide solution/butanol, at an elevated temperature, preferably at the boiling point of the solvent, to obtain the corresponding deacyl-4-phenoxypiperidine, that is to obtain the compound of formula I in which $R^1$ denotes a hydrogen atom.

The alkylation (wherein "alkyl" also includes alkenyl, phenalkyl and cycloalkylmethyl) is carried out, for example, with an alkylating agent $R^4$—X (wherein $R^4$ has its previously-noted meaning and X denotes a leaving group), such as an alkyl halide, an alkyl sulfonate, for example tosylate, or an alkyl sulfate, in inert solvent, such as acetone, methyl ethyl ketone, an alcohol, such as methanol, ethanol or isopropanol, dimethylformamide and the like, or without a solvent, using an auxiliary base, such as sodium carbonate, potassium carbonate or triethylamine, at a temperature of from about 20° to 100° C. The alkylation can also be effected by reacting resulting compounds of formula I (wherein $R^1$ denotes a hydrogen atom) with an acyl derivative $R^5$—CO—X (wherein $R^5$ and X have their previously-ascribed meanings) and subsequently reducing the product. Examples of suitable acyl derivatives are acetyl chloride, propionyl chloride, butyryl chloride, pivaloyl chloride, cyclopropylcarbonyl chloride, cyclobutylcarbonyl chloride, benzoyl chloride and phenylacetyl chloride.

The reduction of resulting compounds of formula I (wherein $R^1$ represents an $R^5$—CO—group and $R^5$ has its previously-stated meaning) is carried out, for example, by reacting the compounds with a complex metal hydride, as reducing agent, in an anhydrous organic solvent and working up the mixture by hydrolysis. Suitable reducing agents are, inter alia, lithium aluminum hydride (lithium hydridoaluminate) and sodium dihydro-bis-(2-methoxyethoxy)aluminate. Suitable solvents are inert anhydrous ethers, such as diethyl ether, tetrahydrofuran, dioxane, 1,2-dimethoxyethane and diethylene glycol diethyl ether, and also aromatic hydrocarbons, such as benzene and toluene, or mixtures of the mentioned compounds. The temperature of the reaction can vary within wide limits, for example from 0° to 100° C. It is usually most appropriate to carry out the reaction at the reflux temperature of the reaction mixture. At the reflux temperature, which is preferred, the reaction usually ends after 3 to 4 hours. The reactants are suitably used in equivalent amounts, but an excess of reducing agent is preferred. After reaction with the reducing agent, the reaction product is worked up by treating the reaction mixture with an aqueous medium, such as water, dilute aqueous inorganic acids or bases or other water-containing media. The product is optionally isolated as a free base or as an acid-addition salt by adjusting the pH value.

The reduction of resulting compounds of formula I (wherein $R^2$ represents a nitro group) to those in which $R^2$ denotes an amino group is carried out, for example, by reacting the compounds with hydrogen in the presence of a metal catalyst, such as Raney nickel, palladium, platinum, platinum-on-charcoal or palladium-on-charcoal, in suitable solvent, for example an alkanol, under a pressure of from 1 to 200 atmospheres, preferably under atmospheric pressure, or by reducing the compounds with hydrazine in the presence of Raney nickel in an alkanol, for example ethanol (see also Houben-Weyl, Volume 11/1, page 360 et seq.). Acylation of the amino group, which optionally follows, is carried out by reacting the product with a corresponding acid anhydride or acid halide (compare, inter alia, Houben-Weyl, Volume 8, page 655).

Reduction of the resulting compounds of formula I (in which $R^2$ denotes an amino group) to those in which $R^2$ represents a hydrogen atom is carried out by diazotizing the amino group to the diazonium group (compare Houben-Weyl, Volume 10/3, page 1 et seq.) and subsequently reducing the diazonium group, for example with zinc or, preferably, with hypophosphorous acid (compare Houben-Weyl, Volume 10/3, page 115 et seq.).

The resulting salts, for example the hydrochlorides, are optionally converted into the corresponding free base by reaction with aqueous sodium hydroxide or potassium hydroxide, and the free base is then isolated by solvent extraction with a suitable water-immiscible solvent, such as chloroform, methylene chloride, diethyl ether, benzene, toluene, cyclohexane and the like. The free bases are alternatively obtained by reacting an acid-addition salt with sodium methylate in methanol and isolating the base. Salts are optionally converted into other salts, for example pharmacologically-acceptable acid-addition salts, by conversion into the base and further reaction with a suitable acid.

Acid-addition salts are obtained by dissolving a 4-phenoxypiperidine in a suitable solvent, for example water, acetone, a low-molecular aliphatic alcohol (ethanol or isopropanol) or an ether (tetrahydrofuran or diethyl ether), which contains the desired acid or to which the desired acid is then added. The salts are isolated by filtration, precipitation with a non-solvent for the acid-addition salts or evaporation of the solvent.

N-oxidation, that is conversion of a resulting base of formula I or of an acid-addition salt thereof into the N-oxide, is preferably carried out with m-chloroperbenzoic acid or an equivalent oxidizing agent, such as monopersulfuric acid, monoperphthalic acid, peracetic acid, trifluoroperacetic acid or perbenzoic acid, the temperature being kept between 0° and 80° C., appropriately at room temperature. A customary inert solvent, for example benzene, toluene, chloroform, methylene chloride or mixtures thereof, is employed as solvent.

The starting compounds of formula II are known or are conventionally prepared by known processes from available starting materials. To prepare a compound of the first or second group of particular embodiments of formula I, corresponding starting compounds II are employed.

These compounds II are of one of the formulae:

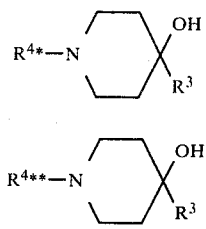

wherein

R³ has its previously-ascribed meaning,

R⁴* denotes a straight-chain alkyl group with from 1 to 3 carbon atoms, a phenylalkyl group with 1 or 2 carbon atoms in the alkyl part or an R⁵*—CO— group, R⁵* denotes a hydrogen atom (—H), an alkyl group with 1 or 2 carbon atoms, a phenyl group or a benzyl group, R⁴ denotes a branched alkyl group with from 3 to 5 carbon atoms, an alkenyl group with from 3 to 5 carbon atoms, a cycloalkylmethyl group with from 3 to 5 carbon atoms in the cycloalkyl part or an R⁵—CO—group, and R⁵** denotes a branched alkyl group with 3 or 4 carbon atoms, an alkenyl group with from 2 to 4 carbon atoms or a cycloalkyl group with from 3 to 5 carbon atoms.

The following examples serve to illustrate the invention without limiting it. "m.p." denotes "melting point". The temperature data are in °C.

EXAMPLE 1

1-Methyl-4-(4-nitrophenoxy)-4-phenylpiperidine

A solution of 54 g of 1-methyl-4-phenylpiperidin-4-ol in 200 ml of absolute dimethylformamide is added dropwise to a suspension of 12.6 g of sodium hydride (80% strength in oil) in 200 ml of absolute dimethylformamide at a temperature of 45° C., while stirring and with exclusion of moisture. During this addition, evolution of hydrogen occurs. When the addition has ended, the mixture is stirred at 50° C. for a further 2 hours and allowed to cool to room temperature. A solution of 49.4 g of 4-fluoronitrobenzene in 100 ml of absolute dimethylformamide is then added dropwise thereto. Stirring is continued for a further 2 hours, and the reaction mixture is then poured onto 800 ml of ice-water. The precipitate which forms is filtered off and washed with water. Recrystallization from 250 ml of ethanol yields 52 g of the title compound of m.p. 135° to 137° C.

EXAMPLE 2

(a) 4-Benzyl-1-methyl-4-(4-nitrophenoxy)piperidine

A solution of 40.0 g of 4-benzyl-1-methylpiperidin-4-ol in 120 ml of absolute dimethylformamide is added dropwise to a suspension of 8.76 g of sodium hydride (80% strength in oil) in 200 ml of absolute dimethylformamide, while stirring and with exclusion of moisture. During this addition, evolution of hydrogen occurs. When the addition has ended, the mixture is stirred at room temperature for 2 hours, 31.6 g of 4-fluoronitrobenzene are added dropwise thereto, and the mixture is stirred at 50° C. for a further 2 hours. The resulting brown reaction mixture is then poured into 350 ml of ice-water and is stirred for 30 minutes; a precipitate (which has separated out) is filtered off and washed with water and petroleum ether. This crude product is dissolved in 150 ml of boiling ethanol, decanted to remove undissolved material, treated with active charcoal and filtered. 100 ml of petroleum ether are added slowly to the cooled filtrate, and the formed precipitate is filtered off and washed with petroleum ether. 38.9 g of the cream-colored title compound of m.p. 116° to 117° C. are obtained by successive concentration of the filtrate.

The following compounds are obtained analogously:

(b) 1-tert.-Butyl-4-(4-nitrophenoxy)-4-phenylpiperidine

[of m.p. 153° to 154° C.]from 1-(tert.-butyl)-4-phenylpiperidin-4-ol and 4-fluoronitrobenzene and (c) 1-isopropyl-4-(4-nitrophenoxy)-4-phenylpiperidine from 1-isopropyl-4-phenylpiperidin-4-ol and 4-fluoronitrobenzene.

EXAMPLE 3

(a) 4-(4-Aminophenoxy)-1-methyl-4-phenylpiperidine 51 g of 1-methyl-4-(4-nitrophenoxy)-4-phenylpiperidine are dissolved in 1.5 liters of ethanol and are hydrogenated under a hydrogen pressure of 1 atmosphere in the presence of platinum. The catalyst is filtered off, the filtrate is concentrated to 300 ml and crystals (which have separated out) are collected. 34.3 g of the title compound of m.p. 173° to 174° C. are obtained by successive concentration of the filtrate.

The following compounds are obtained analogously by hydrogenating the noted starting compounds:

(b) 4-(4-Aminophenoxy)-1-(tert.-butyl)-4-phenylpiperidine from 1-(tert.-butyl)-4-(4-nitrophenoxy)-4-phenylpiperidine, (c) 4-(4-aminophenoxy)-4-benzyl-1-methylpiperidine [of m.p. 118° to 119° C. (ethyl acetate/petroleum ether)] from 4-benzyl-1-methyl-4-(4-nitrophenoxy)-piperidine and (d) 4-(4-aminophenoxy)-4-phenyl-1-(2-phenylethyl)-piperidine from 4-(4-nitrophenoxy)-4-phenyl-1-(2-phenylethyl)-piperidine.

EXAMPLE 4

(a) 1-Methyl-4-phenoxy-4-phenylpiperidine

A solution of 3.0 g of sodium nitrite in 18 ml of water is added dropwise to a solution of 10.0 g of 4-(4-aminophenoxy)-1-methyl-4-phenylpiperidine in 12 ml of concentrated hydrochloric acid and 30 ml of water at −10° C. The mixture is subsequently stirred at −5° C. for 45 minutes, 50 ml of 50% strength hypophosphorous acid are added dropwise at −5° C., and the reaction mixture is left to stand at 0° C. for 24 hours. It is rendered alkaline with 6 N sodium hydroxide solution, while cooling with ice, and extracted with diethyl ether. After treating the organic phase with active charcoal, it is dried over sodium sulfate and concentrated. Resulting residue yields (after recrystallization from 100 ml of n-hexane) 5.5 g of the title compound of m.p. 99° to 101° C.

The following compound is obtained analogously:

(b) 4-Benzyl-1-methyl-4-phenoxypiperidine

[as the hydrochloride of m.p. 197° to 198° C. (from ethanol)] from 4-(4-aminophenoxy)-4-benzyl-1-methylpiperidine.

EXAMPLE 5

(a) 4-Phenoxy-4-phenylpiperidine 9.0 g of 1-methyl-4-phenoxy-4-phenylpiperidine are added in portions of 100 ml of chloroformic acid ethyl ester at 80° C.; severe foaming is observed during this addition. When the addition has ended, the mixture is boiled under reflux for 3 hours, excess chloroformic acid ethyl ester is distilled off in vacuo, and 120 ml of water and 15 ml of concentrated ammonia are added to resulting solid residue. This mixture is stirred thoroughly, and the precipitate is filtered off and rinsed with water. The 1-ethoxycarbonyl-4-phenoxy-4-phenylpiperidine (m.p. 117° to 118° C., from ethanol) thus obtained is boiled under reflux with a solution of 15 g of potassium hydroxide in 150 ml of n-butanol for 4 hours; after cooling, 300 ml of water are added to the solution, and the obtained mixture is extracted twice with diethyl ether. The combined organic phases are dried over sodium sulfate and concentrated. The title compound remains as a brownish oil. The hydrochloride melts at 192° C. (from ethanol).

The following compound is obtained analogously:
(b) 4-(4-Nitrophenoxy)-4-phenylpiperidine
(oil), from 1-methyl-4-(4-nitrophenoxy)-4-phenylpiperidine, intermediate 1-ethoxycarbonyl-4-(4-nitrophenoxy)-4-phenylpiperidine of m.p. 137° to 138° C.

EXAMPLE 6

(a) 1-Isopropyl-4-(4-nitrophenoxy)-4-phenylpiperidine 6.0 g of 4-(4-nitrophenoxy)-4-phenylpiperidine, 2.8 g of potassium carbonate and 3.0 g of isopropyl bromide are boiled under reflux in 50 ml of ethyl methyl ketone for 24 hours. The solvent is evaporated off, the residue is taken up in 100 ml of water, and the aqueous mixture is extracted with 100 ml of diethyl ether. The organic phase is dried over sodium sulfate, filtered over active charcoal and concentrated. 5.2 g of the title compound remain as a viscous, pale yellow oil.

The following compounds are obtained analogously:
(b) 1-Allyl-4-(4-nitrophenoxy)-4-phenylpiperidine
from 4-(4-nitrophenoxy)-4-phenylpiperidine and allyl bromide and
(c) 4-(4-nitrophenoxy)-4-phenyl-1-(2-phenylethyl)-piperidine
from 4-(4-nitrophenoxy)-4-phenylpiperidine and 2-phenylethyl bromide.

EXAMPLE 7

(a) 1-Cyclopropylmethyl-4-phenoxy-4-phenylpiperidine 1. 2.1 g of cyclopropanecarboxylic acid chloride in 5 ml of methylene chloride are added dropwise to a solution of 5.06 g of 4-phenoxy-4-phenylpiperidine and 2.5 g of triethylamine in 50 ml of methylene chloride at from 0° to 8° C. The mixture is stirred at 0° C. for 2 hours, water is added, the organic phase is separated off, extraction is again carried out with methylene chloride, and the combined organic phases are washed with dilute hydrochloric acid and sodium carbonate solution, dried over sodium sulfate and concentrated. The oily residue (1-cyclopropylcarbonyl-4-phenoxy-4-phenylpiperidine) is dissolved in 50 ml of tetrahydrofuran, 0.75 g of lithium aluminum hydride is added carefully in portions, and the mixture is then boiled under reflux for 1 hour. After cooling, 50 ml of water are first added dropwise, and the mixture is extracted twice (with 50 ml of diethyl ether each time). After drying the combined organic phases, the solvent is distilled off. 4.6 g of the title compound remain as a pale yellow viscous oil.

2. Alternatively, the title compound is obtained by alkylating 4-phenoxy-4-phenylpiperidine with cyclopropylmethyl bromide analogously to Example 6(a).

The following compound is obtained analogously:
(b) 1-(2,2-Dimethyl-1-propyl)-4-phenoxy-4-phenylpiperidine
1. from 4-phenoxy-4-phenylpiperidine and pivaloyl chloride, with subsequent reduction of the intermediate product, 4-phenoxy-4-phenyl-1-pivaloylpiperidine, with lithium aluminum hydride, or, alternatively,
2. from 4-phenoxy-4-phenylpiperidine and neopentyl bromide analogously to Example 6(a).

EXAMPLE 8

(a) 4-(4-Acetaminophenoxy)-1-methyl-4-phenylpiperidine

A solution of 0.85 g of acetyl chloride in 5 ml of benzene is added dropwise to a solution of 2.8 g of 4-(4-aminophenoxy)-1-methyl-4-phenylpiperidine and 1.1 g of triethylamine in 10 ml of benzene. After stirring the mixture at room temperature for 6 hours, it is concentrated; the resulting residue is taken up with 30 ml each of water and diethyl ether; the obtained mixture is shaken thoroughly, and the organic phase is separated off, dried over sodium sulfate and concentrated. 2.8 g of the title compound remain as a viscous yellow oil which crystallizes (m.p. 143° to 144° C.) from diethylether after standing for several days.

The following compound is obtained analogously:
(b) 1-Methyl-4-phenyl-4-(4-pivaloylaminophenoxy)-piperidine
from 4-(4-aminophenoxy)-1-methyl-4-phenylpiperidine and pivaloyl chloride.

EXAMPLE 9

1-Methyl-4-phenoxy-4-phenylpiperidine N-oxide 1.5 g of 1-methyl-4-phenoxy-4-phenylpiperidine are dissolved in 4 ml of methanol, and 1.7 g of 80% strength m-chloroperbenzoic acid, dissolved in methanol, are added slowly thereto while cooling with ice. After stirring the mixture at room temperature for 3 hours, the solvent is stripped off and the residue is partitioned between concentrated sodium hydroxide solution and chloroform. The crude N-oxide hydrate (which remains after drying the chloroform phase and evaporating off the solvent) is taken up in a little methanol, and the equivalent amount of methanolic fumaric acid is added. 1 g of a colorless precipitate is obtained.

The use of ethereal hydrochloric acid instead of methanolic fumaric acid gives the hydrochloride.

EXAMPLE 10

Tablets 4-(4-Aminophenoxy)-1-methyl-4-phenylpiperidine (10 kg), lactose (75 kg), maize starch (80 kg), highly disperse silicic acid (3 kg) and sodium lauryl-sulfate (4 kg) are sieved and mixed. Polyvinylpyrrolidone (average molecular weight: 25,000; 5 kg) is dissolved in 20 l of water and the powder mixture is moistened thoroughly with this solution. The moist mixture is granulated through a sieve of 1.2 mm mesh width. After drying the granules, sodium carboxymethylcellulose (16 kg), talc (5 kg) and magnesium stearate (2 kg) are admixed. The finished mixture is pressed to form tablets with a diameter of 8 mm and weighing 200 mg.

Instead of the 4-(4-aminophenoxy)-1-methyl-4-phenylpiperidine, an equivalent amount of another compound of formula I, for example 1-methyl-4-phenoxy-4-phenylpiperidine, or such a compound in the form of a physiologically-acceptable salt or N-oxide is optionally used as the active tablet ingredient.

EXAMPLE 11

Capsules 4-(4-Aminophenoxy)-1-methyl-4-phenylpiperidine (10 kg) and lactose (spray-dried, 210 kg) are mixed, and the mixture is filled into capsules of capsule size 3.

EXAMPLE 12

Ampoules

1-Methyl-4-phenoxy-4-phenylpiperidine hydrochloride (2,500 kg) and mannitol (4,000 kg) are dissolved in 80 liters of doubly-distilled water, and the solution is made up to 100 liters with doubly-distilled water. The solution is filtered through a membrane filter with a pore diameter of $0.1\mu$, filled into 2-ml ampoules and sterilized at 100° C. for 1 hour.

Pharmacology

The pronounced antiptotic and analgesic properties of the compounds according to the invention are demonstrated by several model experiments in which the 4-phenoxypiperidines prove to be superior to the commercially-available antidepressant, imipramine, as a result of their more powerful action, their longer period of action and their analgesic component.

The comparison of the antiptotic and analgesic properties of the compounds according to the invention and those of imipramine was carried out using the compounds listed in Table I as examples.

TABLE I

1. Imipramine
2. 1-Methyl-4-phenoxy-4-phenylpiperidine
3. 1-Methyl-4-(4-nitrophenoxy)-4-phenylpiperidine
4. 4-(4-Aminophenoxy)-4-benzyl-1-methylpiperidine
5. 4-(4-Aminophenoxy)-1-methyl-4-phenylpiperidine
6. 4-Benzyl-1-methyl-4-(4-nitrophenoxy)piperidine
7. 4-Benzyl-1-methyl-4-phenoxypiperidine
8. 4-Phenoxy-4-phenylpiperidine
9. 1-(tert.-Butyl)-4-(4-nitrophenoxy)-4-phenylpiperidine
10. 4-(4-Acetaminophenoxy)-1-methyl-4-phenylpiperidine Table II shows the $LD_{50}$ values determined after oral administration and the $ED_{50}$ values obtained in the various tests after oral administration (mg/kg in each case).

The pharmacological properties were established in accordance with the following methods.

All the experiments are carried out on female albino mice NMRI of 20 to 30 g body weight. 5 to 20 animals are employed per dose and the dose/response relationship are determined.

Antiptotic action (Reserpine antagonism)

Subcutaneous administration of 2 mg/kg of reserpine to albino mice causes ptosis in the course of several hours [Reserpine Ptosis, Domenjoz and Theobald (1959), *Arch. Int. Pharmacodyn.* 120,450]. The test substances are administered to the animals orally in various doses 3 hours before the administration of reserpine. The intensity of ptosis is graded by a rating scale 3-2-1-0 (complete, moderate, slight, no ptosis) in the 2nd, 3rd and 4th hour after administration of the reserpine (that is 5, 6 and 7 hours after administration of the substance). The substances tested antagonize the ptosis according to the dose. The $ED_{50}$ of the antagonistic action is evaluated in comparison to the daily reserpine control.

Analgesia (a) Tail flick test: Albino mice are exposed to thermal pain, from a focused heat ray, at the tail root, and the time which elapses before the tail is drawn away is recorded. This time is usually in the range of from 4 to 5 seconds. The substances tested cause a delayed reaction to the thermal pain, that is a reduced thermal pain reaction. The dose which prolongs the reaction time by 50% is determined. Literature: D'Amour, F. E., and Smith, D. L., (1941) *J. Pharmacol. Exp. Ther.* 72, 74.

(b) Writhing test (acetic acid writhing): intraperitoneal injection of 0.2 ml/20 g of body weight of mouse of a 0.75% strength acetic acid solution induces in albino mice a typical syndrome proceeding over the body with dorsal flection, called "writhing". These "writhes" (occurring in the course of the first half hour after administration) are counted over a period of 5 to 20 minutes after administration of acetic acid. The substances tested (administered 30 minutes before the acetic acid injection) cause a reduction in the number of writhing syndromes. The dose which reduces the number thereof by 50%, relative to the daily control, is determined. Literature: Koster, Anderson, de Beer (1959) Fed.Proc. 18, 412.

(c) Administration of naloxone (2 mg/kg, subcutaneously) 25 minutes after administration of the test substances is capable of antagonizing analgesic actions. The

| | Antiptotic action Reserpine antagonism $ED_{50}$ | | | Analgesic action | | | | |
|---|---|---|---|---|---|---|---|---|
| | | | | tail flick test | | Acetic acid writhing test | | Acute toxicity |
| Serial No. | 5 hours | 6 hours | 7 hours | $ED_{50}$ | N | $ED_{50}$ | N | $LD_{50}$ |
| | after administration | | | | | | | |
| 1 | 18 | 50 | 100 | >50 | | >100 | φ | 470 |
| 2 | 2.1 | 2.7 | 4.0 | 35 | + | | | 220 |
| 3 | 0.7 | 2.0 | 5.8 | 50 | | | | 140 |
| 4 | 9.5 | 24 | 50 | 2 | (+) | 27 | (+) | 180 |
| 5 | 0.7 | 3.0 | 10 | 12 | + | 7 | + | 160 |
| 6 | | | | >75 | | 35 | | 290 |
| 7 | | | | 55 | | 27 | | 300 |
| 8 | ~25 | >50 | >50 | 25 | | 50 | | >200 |
| 9 | | | | | | 10 | + | |
| 10 | <10 | <10 | <10 | 12,5 | | 10 | (+) | between 100–200 | symbols +, (+) and φ in the table, column N, denote total, moderate or no naloxone antagonism.

Determination of the lethal effect

The mice were given food (Altromin ®) and water ad libitum. The substances to be tested were administered orally as solutions of varying concentration in a volume of from 10 to 20 ml/kg using a stomach tube; 5 animals per dose were kept in Macrolon cages, type II. The observation time was 7 days. The LD$_{50}$, that is the dose at which 50% of the animals died, was determined graphically from the dose/response curve. Literature: Litchfield and Wilkoxon (1946) *J. Pharm. Exp. Therap.* 96/2, 99.

The invention and its advantages are readily understood from the foregoing description. It is apparent that various changes may be made in the synthesis, the intermediates, the essential active ingredients, the compositions and the method of use without departing from the spirit and scope of the invention or sacrificing its material advantages. The various noted aspects hereinbefore described are merely illustrative of preferred embodiments of the invention.

What is claimed is:

1. A compound selected from the group consisting of (a) a 4-phenoxypiperidine of the formula

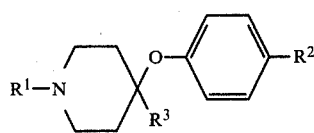

(I)

wherein
R$_1$ is —H, C$_{1-5}$ alkyl, C$_{3-5}$ alkenyl, cycloalkylmethyl with from 3 to 7 ring carbon atoms or phenylalkyl with from 1 to 3 carbon atoms in the alkyl,
R$^2$ is —H, —NO$_2$, amino or (carboxylic acid or carbonic acid acyl)amino and
R$^3$ is phenyl or benzyl,
(b) an N-oxide of (a) and
(c) an acid-addition salt of (a).

2. A free base according to claim 1.
3. An N-oxide according to claim 1.
4. A physiologically-acceptable acid-addition salt according to claim 1.
5. A compound according to claim 1 wherein
R$^1$ is —H, straight-chain alkyl with from 1 to 3 carbon atoms or phenylalkyl with 1 or 2 carbon atoms in the alkyl,
R$^2$ is —H, —NO$_2$, amino or alkylcarbonylamino with from 1 to 5 carbon atoms in the alkyl part, and
R$^3$ is phenyl or benzyl.
6. A compound according to claim 1 wherein
R$^1$ is —H, methyl or benzyl,
R$^2$ is —H, —NO$_2$ or amino, and
R$^3$ is phenyl or benzyl.
7. A compound according to claim 6 wherein R$^3$ is phenyl.
8. A compound according to claim 7 wherein R$^2$ is —NH$_2$.
9. A compound according to claim 1 wherein
R$^1$ is branched alkyl with from 3 to 5 carbon atoms, alkenyl with from 3 to 5 carbon atoms or cycloalkylmethyl with from 3 to 5 ring carbon atoms,
R$^2$ is —H, —NO$_2$, amino or alkylcarbonylamino with from 1 to 5 carbon atoms in the alkyl part, and
R$^3$ is phenyl or benzyl.
10. A compound according to claim 9 wherein
R$^1$ is branched alkyl with from 3 to 5 carbon atoms, allyl or cyclopropylmethyl, and
R$^2$ is —H, —NO$_2$ or amino.
11. A compound according to claim 10 wherein
R$^1$ is isopropyl or tert.-butyl and
R$^3$ is phenyl.
12. A compound according to claim 1 wherein R$^3$ is benzyl.
13. A compound according to claim 1 wherein R$^2$ is —H.
14. A compound according to claim 1 wherein R$^2$ is nitro.
15. A compound according to claim 1 wherein R$^2$ is amino.
16. The compound according to claim 1 which is 1-methyl-4-phenoxy-4-phenylpiperidine.
17. The compound according to claim 1 which is 1-methyl-4-(4-nitrophenoxy)-4-phenylpiperidine.
18. The compound according to claim 1 which is 4-(4-aminophenoxy)-4-benzyl-1-methylpiperidine.
19. The compound according to claim 1 which is 4-(4-aminophenoxy)-1-methyl-4-phenylpiperidine.
20. A pharmacologically-acceptable acid-addition salt of the compound according to claim 19.
21. The compound according to claim 1 which is 4-(4-acetaminophenoxy)-1-methyl-4-phenylpiperidine.
22. A medicament composition useful for treating depression or pain and in which active ingredient is in combination with a pharmaceutical excipient, the active ingredient being from 5 to 95 percent by weight of the composition and comprising at least one pharmacologically-acceptable compound according to claim 1.
23. A medicament composition according to claim 22 which has, per unit dose, from 3 to 15 milligrams of the pharmacologically-acceptable compound.
24. A medicament composition according to claim 22 wherein the pharmacologically-acceptable compound is 4-(4-aminophenoxy)-1-methyl-4-phenylpiperidine or a pharmacologically-acceptable acid-addition salt thereof.
25. An antiptotic and analgesic medicament composition in which active ingredient is in combination with a pharmaceutical excipient, the active ingredient being from 5 to 95 percent by weight of the composition and comprising an effective amount of a physiologically-acceptable compound according to claim 1.
26. A process for treating depression which comprises administering a therapeutically-effective and pharmacologically-acceptable amount of a physiologically-acceptable compound according to claim 1 to a mammal afflicted with or subject to depression.
27. A process for treating pain which comprises administering an analgesically-effective and pharmacologically-acceptable amount of a physiologically-acceptable compound according to claim 1 to a mammal afflicted with pain.
28. A process for treating depression or pain which comprises administering a therapeutically-effective and pharmacologically-acceptable amount of 4-(4-aminophenoxy)-1-methyl-4-phenylpiperidine or a pharmacologically-acceptable acid-addition salt thereof to a mammal afflicted with or subject to depression or afflicted with pain.

* * * * *

UNITED STATES PATENT AND TRADEMARK OFFICE
CERTIFICATE OF CORRECTION

PATENT NO. : 4,333,942
DATED : June 8, 1982
INVENTOR(S) : Klaus EISTETTER, Hans-Peter KLEY, Heinz-Günter MENGE and Hartmann SCHAEFER It is certified that error appears in the above-identified patent and that said Letters Patent are hereby corrected as shown below:

Column 8, line 7, "(b)" should read --b)--. Column 12, line 9, "1-tert.-" should read --1-(tert.- --. Column 13, line 46, start a new line after "dine". Column 15, line 49, insert the following as the heading for Table II --TABLE II  Antiptotic and analgesic action and acute toxicity of 4-phenoxypiperidines in comparison with imipramine; $ED_{50}$ and $LD_{50}$ values after oral administration in [mg/kg] N: naloxone antagonism (+ total ⊕ moderate ∅ non-existent)--. Column 16, line 2, "methods" should read --methods:--; line 12, "*Arch,*" should read --*Arch.*--. Column 17, line 35, "$R_1$" should read --$R^1$--.

Signed and Sealed this

Fifth Day of October 1982

[SEAL]

Attest:

GERALD J. MOSSINGHOFF

Attesting Officer          Commissioner of Patents and Trademarks